United States Patent [19]

Silverstein

[11] 3,982,545
[45] Sept. 28, 1976

[54] MIDDLE EAR AERATION AND IMPLANT

[76] Inventor: Herbert Silverstein, 269 Barwynne, Wynnwood, Pa.

[22] Filed: Oct. 24, 1975

[21] Appl. No.: 625,957

Related U.S. Application Data

[63] Continuation of Ser. No. 499,630, Aug. 22, 1974, abandoned, which is a continuation of Ser. No. 354,523, April 26, 1973, abandoned, which is a continuation of Ser. No. 118,275, Feb. 24, 1971, abandoned.

[52] U.S. Cl................................. 128/350 R; 3/1; 128/DIG. 21
[51] Int. Cl.²................. A61M 27/00; A61F 11/00
[58] Field of Search........... 3/1; 128/350 R, DIG. 21

[56] References Cited
OTHER PUBLICATIONS

"Silastic Artificial Eustachian Tube" by James W. Donaldson, The Bulletin of the Dow Corning Center for Aid to Medical Research, vol. 7, No. 1, Midland, Mich. Jan. 1965, p. 2.
"Teflon Feuerstein Split-Tube", Micro-Surgery Instruments and Implants (Catalog), Richards Mfg. Co., Memphis, Tenn. 1966.

Christopher's Textbook of Surgery, 8th Edition, 1964, pp. 241–242.

*Primary Examiner*—Ronald L. Frinks

[57] ABSTRACT

Methods and an implant are disclosed for aerating the middle ear. The method requires the drilling of a hole in the bony external canal in a zone where the hole will be in communication with the middle ear either directly or through the mastoid air-cell system. The implant is formed from an inert, resiliently flexible material such as silicone rubber and includes a tubular portion and a flange at the posterior end thereof. The tubular portion is dimensioned to be a snug fit in the drilled hole and the flange is relatively large with its thickness and the wall thickness of the tubular portion being such as to enable the flanged end of the implant to be forced through the drilled hole with the flange then springing back into its normal position. The anterior end of the tubular portion is then pulled outwardly to seat the flange against the posterior surface of the bone structure.

4 Claims, 5 Drawing Figures

INVENTOR
HERBERT SILVERSTEIN
BY
ATTORNEY

MIDDLE EAR AERATION AND IMPLANT

The present invention relates to middle ear aeration and to implants for effecting the same and the present application is a continuation of Ser. No. 499,630, filed Aug. 22, 1974 and now abandoned, which was a continuation of Ser. No. 354,523, filed Apr. 26, 1973 and now abandoned, which was a continuation of Ser. No. 118,275 filed Feb. 24, 1971 and now abandoned.

BACKGROUND OF THE INVENTION

It has been recognized for some time that the successful treatment of such cases as persistent serous otitis media, adhesive otitis media, and certain types of chronic suppurative otitis media required some means of permanently aerating the middle ear. As a consequence, a procedure was developed in accordance with which pressure-equalizing tubes were inserted through or beneath the tympanic membranes. Various pressure-equalizing tubes are available but, unfortunately, most of them are soon extruded.

THE PRESENT INVENTION

A principal objective of the present invention is, accordingly, to provide a basis of permanent middle ear aeration, an objective attained by drilling a hole through the bony external canal where it will be in communication with the middle ear and by inserting an implant through the drilled hole that will be self-anchoring against extruding forces.

Another principal objective of the invention is to provide an implant that is adapted for use in the above-summarized method, an objective attained with an implant of an inert, flexibly resilient material and having a tubular portion dimensioned to be a tight fit in the drilled hole and a flange at the posterior end of the tubular portion whose diameter is at least twice that of the tubular portion and with the flange thickness and the wall thickness of the tubular portion being such that the flanged end of the implant may be collapsed and readily forced through the drilled hole. Once the flange clears the bone structure, it returns to its original position and when the anterior end of the tubular portion is pulled outwardly, the flange seats against the posterior surface of the bone structure. While the implant may be withdrawn, the relatively large flange area makes it effectively resistant to extruding forces.

In the accompanying drawings, an embodiment of the implant and alternate surgical procedures are shown as illustrative of these and other of the objectives of the invention and the novel features and advantages thereof.

Figure 2:
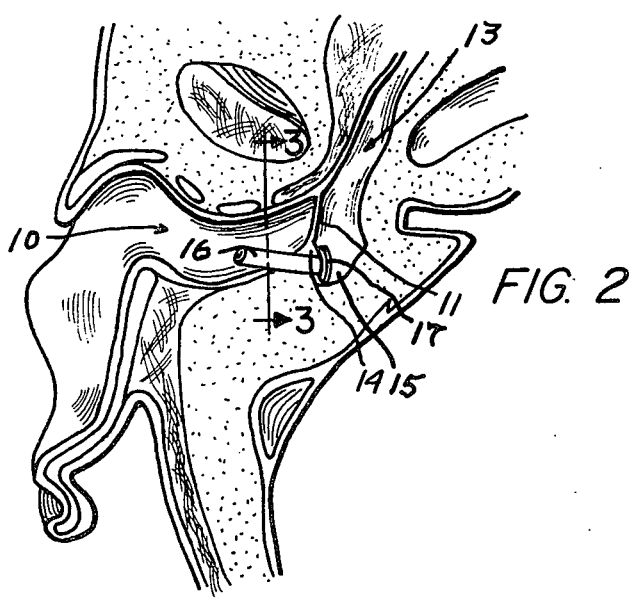
FIG. 2 is a fragmentary section taken vertically thereof on an increase in scale, showing one position of the implant.
Figure 4:
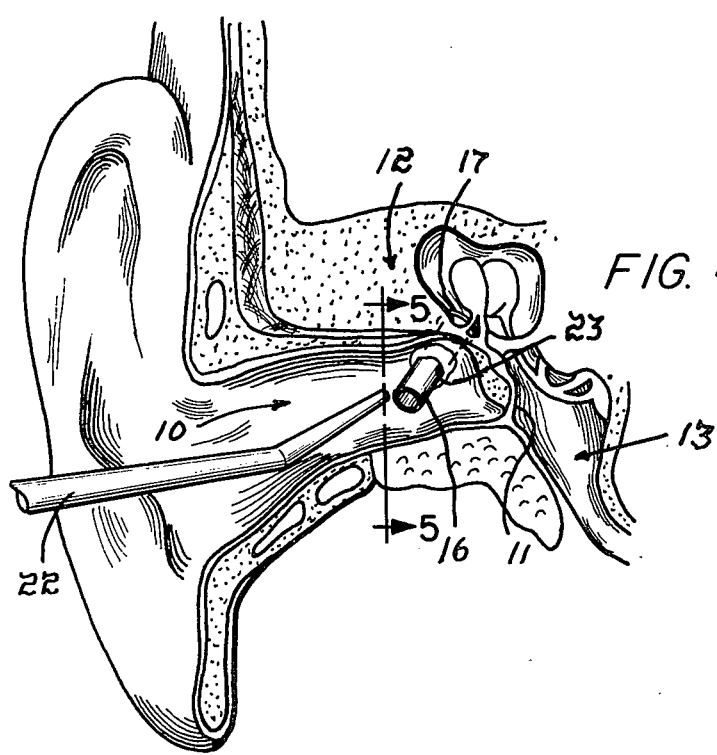
FIG. 4 is a view taken approximately along the indicated lines 4—4 of FIG. 1 showing another position of the implant.

Reference is first made to FIGS. 2 and 4 wherein the external canal is indicated at 10, the tympanic membrane at 11, and the mastoid air cell system at 12. It is, of course, well known that the mastoid air cell system is in communication with the middle ear 13. Normally the bony annulus has an overhang 14 anteriorly of the facial recess 15.

In the aeration of the middle ear in accordance with the invention, a tube 16 having an outwardly disposed end flange 17 is employed. The tube material must be substantially inert and resiliently flexible and silicone rubber tubes have been found satisfactory in use. In practice the tube has an outside diameter of 1.5 m.m. and its flange is relatively large measuring 3.5 m.m. in diameter and 0.25 m.m. in thickness. The wall thickness of the tube is 0.25 m.m. A satisfactory tube length is 1.5 cm.

Figure 1:
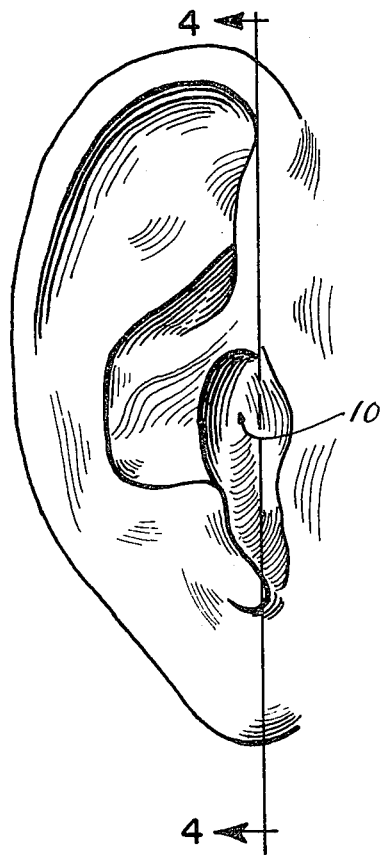
FIG. 1 is an elevational view of an ear as seen from the right hand side of the head.
Figure 3:
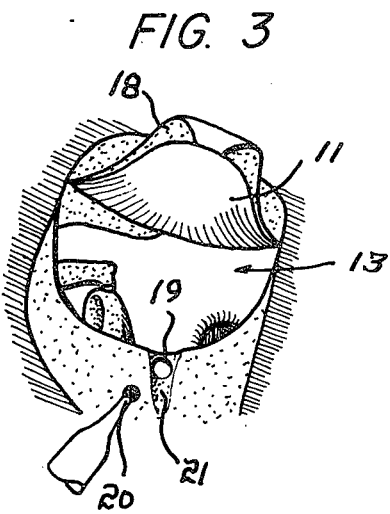
FIG. 3 is a somewhat schematic view taken approximately along the indicated lines 3—3 of FIG. 2 on a further increase in scale.

In practice, see FIG. 3, a tympanomeatal flap 18 is elevated to expose the middle ear structure. After middle ear effusions have been aspirated and the presence of a sufficient bony overhang 14 determined by palpation, a hole 19 is drilled therethrough into the facial recess with a 1.5 mm. burr 20. Desirably, the bone of the canal wall is saucerized to the level of the bony annulus as at 21 using the same burr size.

The flanged end of the tube 16 is then introduced into the hole 19 and forced therethrough as by means of a spatula 22. Once the flange 17 clears the bony structure, it assumes its normal shape and the tube 16 is then pulled outwardly until resistance is felt, other than that due to the tight fit of the tube 16, indicating that the flange 17 has become seated against the posterior wall of the bony structure. Following irrigation, the flap 18 is repositioned. Suction on the tube 16 can be employed to draw the tympanic membrane 11 inwardly into position. The flap 18 is then held in place as by means of small strips of silk and a rubber sponge.

Figure 5:
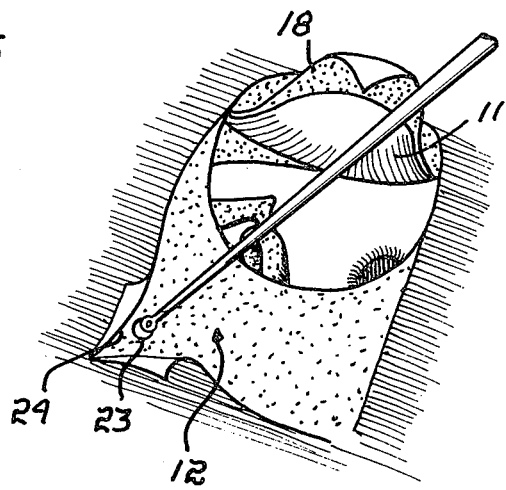
FIG. 5 is another somewhat schematic view taken along the indicated lines 5—5 of FIG. 4.

The above procedure is preferred but if it is determined that the facial recess is too small or the bony overhang has been removed at previous surgery, then a 1.5 mm. hole 23 may be drilled into the mastoid antrum, see FIGS. 4 and 5. The method, in this case, involves, after the tympanomeatal flap 18 has been elevated a separate incision 24 approximately 4 mm. in length in the posterior superior meatal wall skin. The edges of this incision are elevated exposing the bony canal wall and with a 1.5 mm. burr the hole 23 is drilled into the mastoid air cells approximately 7 or 8 mm. from the bony annulus and posterior to the long process of the incus 25 with the burr axis angles posteriorly and superiorly.

The tube 16 is then inserted and the surgery completed in the manner previously described with the additional step of repositioning the flaps created by the incision 24.

The packings, silk strips and sponge, are removed in a week and the tube tested and if occluded, it may be opened by means of a stylet.

From the foregoing, it will be appreciated that the relative dimensions of the tube 16 and its flange 17 are critical for the tube wall and flange thickness ensures that the flanged end of the tube may be introduced through a hole in which the tube itself is a tight fit while permitting the flange 17 to be relatively large as it must be to ensure against its becoming extruded. The life of the tubes cannot at this time be determined but at the present time, the oldest has been functioning satisfactorily for more than 2 years.

I claim:

1. A middle ear aeration implant for insertion through a hole drilled through the wall of the bony external canal in an area in which it is in communication with the middle ear and of a diameter in the order of 1.5 mm in diameter, said implant being of a resiliently yieldable inert elastomeric material having the characteristics of silicone rubber and comprising a tubular portion of a length substantially greater than the axial extent of the hole and of an outside diameter such as to be a snug fit in said hole and a flange at the posterior end of the tubular portion that is of a diameter in the neighborhood of 3.5 mm and in a plane at right angles to the axis thereof, the thickness of the flange and of the wall of the tubular portion being in the order of 0.25 mm thereby to enable the flange to be collapsed against the tubular portion and the length of the tubular portion being in the order of 1.5 cm. thereby to enable the flange to be collapsed against the tubular portion and the length of the tubular portion against which the flange is collapsed itself so collapsed that the thus collapsed part of the implant is of a cross sectional size and shape so closely approximating said outside diameter and also sufficiently stiff that it may be forced through said hole without damaging the bony structure with the anterior end of the implant protruding outwardly and with the resiliency of the material restoring the flange to its normal position, once the collapsed flange clears the bony structure, whereby when a pull is exerted at the anterior end of the implant, the flange is seated against the posterior surface of the bony structure with the snug fit of the tubular portion frictionally holding it against posterior movement.

2. The method of effecting middle ear aeration that comprises the steps of elevating the skin of the external canal including the tympanic membrane, and drilling a hole through the bony external canal in an area where it will be in communication with the middle ear, forming an implant of a flexibly resilient inert plastic material to provide a tubular portion of a diameter that will ensure a snug fit in the hole and a flange at the posterior end of the tubular portion that is at least twice the diameter of the tubular portion, forcing the flanged end of the implant through the hole with the yielding quality of the material permitting the collapse of said flanged end to the necessary extent and the resilient quality of the material restoring the flange to its normal position once the bony structure is cleared, and then exerting a pull on the anterior end of the tubular portion of the implant to seat the flange against the posterior surface of the bony structure.

3. The method of claim 2 in which the hole is drilled through the long overhang of the facial recess.

4. The method of claim 2 in which the hole is drilled into the mastoid antrum.

* * * * *